United States Patent [19]

Levy et al.

[11] Patent Number: 5,095,033

[45] Date of Patent: Mar. 10, 1992

[54] METHOD FOR TREATING EPILEPSY

[75] Inventors: René H. Levy, Seattle; Joan S. Lockard, Bellevue; Richard H. Finnell, Pullman, all of Wash.; Bernard M. Hublot, Compiegne; Jacques A. Tor, Elincourt-Sainte-Marguerite, both of France

[73] Assignee: Laboratoires Biocodex, Montrouge Cedex, France

[21] Appl. No.: 662,825

[22] Filed: Mar. 1, 1991

[51] Int. Cl.$^5$ ............................................. A61K 31/36
[52] U.S. Cl. ..................................................... 514/464
[58] Field of Search ......................................... 514/464

[56] References Cited

U.S. PATENT DOCUMENTS 3,910,959  10/1975  Vallet ................................... 549/445

Primary Examiner—Stanley J. Friedman
Attorney, Agent, or Firm—Wegner, Cantor, Mueller & Player

[57] ABSTRACT

A method for treating epilepsy in humans which comprises administering stiripentol to a patient under antiepileptic treatment with usual drugs in order to alleviate or prevent side effects. The invention also provides an antiepileptic composition comprising stiripentol.

3 Claims, No Drawings

METHOD FOR TREATING EPILEPSY

BACKGROUND OF THE INVENTION

Epileptic patients faced three successive curses before reaching their present medical status, which is reasonably comfortable for a majority of them. The first one was that epileptic seizures were not considered an illness, but supernatural, awe-inspiring phenomena. It took many centuries for epilepsy to be included in the clinical field, and recent evaluations of the sociological problems encountered by epileptic patients show that some difficulties are still lingering.

The second move was to find a treatment. In the works of C. B. RADCLIFFE, "the name of Sir Charles LOCOCK ought to be remembered with gratitude by every epileptic" (Radcliffe C. B.—Epilepsy and other convulsive affections of the nervous system. Their pathology and treatment. London, J. Churchill, 1881), since he proposed the use of bromides in 1857, successfully but at the price of considerable side-effects.

This became the third curse on an illness duly recognized as such, with a fair number of active remedies, namely valproic acid, phenytoin and carbamazepine, none of them being devoid of side-effects sometimes painful, to the point of almost including iatrogenic symptom, "mental viscosity" or "glischroidy" in its duly barbiturised patients' descriptions.

One of the most disturbing of these unwanted effects is the "risk of major malformations, minor anomalies and developmental disturbances in the fetus or infant" of epileptic mothers. Hence the "Guidelines for the Care of Epileptic Women of Childbearing Age, of the Commission on Genetics, Pregnancy, and the Child, of the International League Against Epilepsy" (Epilepsia, 1989, 30, 409-410).

The present invention relates to the use of stiripentol to counteract such a risk.

Stiripentol (INN), or 1-(3,4-methylenedioxyphenyl)-4,4-dimethylpent-1-en-3-ol has been disclosed in U.S. Pat. No. 3,910,959 (Vallet) as a CNS drug, and further was proposed for the treatment of epilepsy (Loiseau P. and Duché B. in Antiepileptic Drugs, Third Edition edited by R. Levy et al, Raven Press, New York, 1989; Vincent J. C. in New Anticonvulsant Drugs, Edited by B. S. Meldrum and R. J. Porter, John Libbey, London, 1986).

If has now been found that stiripentol alleviates or prevents some major undesired effects and phenomena caused by the usual antiepileptic drugs. For example, while all major antiepileptic drugs are teratogens or pro-teratogens (Teratogenicity of Antiepileptic Drugs: Analysis of Possible Risk Factors by Kaneko et al., Epilepsia, 29: 459-467 (1988); Teratogenicity of Antiepileptic Drug Combinations with Special Emphasis on Epoxide (of Carbamazepine) by Lindhout et al. Epilepsia, 25: 77-83 (1984); Fetal Hydantoin Syndrome by James W. M. Hanson, Teratology, 13: 185-188, 1976), stiripentol is an antiepileptic drug capable of decreasing or eliminating the teratogenicity associated with those drugs.

DETAILED DESCRIPTION OF THE INVENTION

An object of the invention is a method for treating epilepsy in humans which comprises administering a therapeutically effective dose of stiripentol to a patient under antiepileptic treatment, in order to alleviate or prevent the side effects of the drugs used in said antiepileptic treatment.

A more specific object of the invention is a method for treating epilepsy in a woman patient which comprises administering a therapeutically effective dose of stiripentol to said woman patient submitted to antiepileptic treatment, in order to fight against teratogenic effects of the drugs used in said anti-epileptic treatment.

Stiripentol is particularly useful in the treatment of patients receiving phenytoin, carbamazepine, valproic acid, sodium valproate, and the like, especially phenytoin.

Stiripentol may be administered at a daily dosage level of 5-100 mg/kg, particularly 10-50 mg/kg, namely by the oral route.

A further object of the invention is an anticonvulsant or antiepileptic composition containing in combination or separately a therapeutically effective amount of stiripentol and a therapeutically effective amount of an anticonvulsant or antiepileptic drug. The composition is preferably in a form suitable for oral administration, i.e. tablets, capsules, dragees or syrups.

A preferred composition contains an oral unit dose of 100–500 mg of stiripentol.

A further preferred composition is in the form of oral unit doses containing 100–500 mg of stiripentol and 100 mg of phenytoin.

Another preferred composition is in the form of oral unit doses of 100–500 mg of stiripentol and 200–500 mg of valproic acid or sodium valproate.

Another preferred composition is in the form of oral unit doses of 100–500 mg of stiripentol and 100–400 mg of carbamazepine.

The following examples are provided to illustrate the invention.

EXAMPLE 1

Summary of Teratology Studies: Phenytoin and Stiripentol

I. Materials and Methods

Three highly inbred mouse trains (SWV, LM/Bc and C57BL/6J) were chronically administered the test compounds for two weeks prior to the first attempts at mating. Stiripentol was mixed with ground rodent chow and repelleted to be administered in the animal's feed, while phenytoin was administered in the animal's drinking water. During this two week pre-treatment, the animals were bled from the retroorbital sinus at days 7 and 14, and plasma drug concentrations were determined to ensure that the dams were all within the desired therapeutic range of the test compound. The treatment groups for this study are depicted in Table 1. Each treatment group consisted of 10 dams from each of the three test mouse strains. The dams continued to receive the experimental treatment throughout the pregnancy. On gestational day 18, the dam was sacrificed and the fetuses removed. The location and position of all viable fetuses and resorption sites were recorded. Those fetuses that failed to show any spontaneous or elicited movements were regarded as dead and included amongst the resorptions for the statistical analyses. Viable fetuses were weighed, sexed, and examined for gross external malformations. Following euthanasia, one-third of the fetuses were randomly placed in 95% alcohol for alizarin red skeletal staining, and the remaining fetuses were placed in Bouin's fixative in preparation for examination of internal malformations using Wilson's freehand razor blade technique. The 0.05 level of significance was set for all statistical analyses. The mean difference between measurements were tested using both two-way and three-way analysis of variance following arc-sin transformation of the data where appropriate. Where differences were found to be significant, a Tukey pairwise comparison test was performed. Stiripentol and phenytoin were assayed by HPLC.

II. Experimental Treatment Groups

The study was conducted in two parts which are referred to as year I and year II (in table 2 and in the text). Groups 1 through 6 were included in year I and year II while group 7 was added in year II to determine whether stiripentol co-treatment would be protective against the teratogenicity associated with a high dose of phenytoin (60 mg/Kg).

TABLE 1

| Group 1. | Stiripentol (200 mg/kg) |
| --- | --- |
| Group 2. | Control pair fed to Group 1 |
| Group 3. | Phenytoin (30 mg/kg) |
| Group 4. | Phenytoin (60 mg/kg) |
| Group 5. | pH 10.3 water control |
| Group 6. | Stiripentol (200 mg/kg) plus Phenytoin (30 mg/kg) |
| Group 7. | Stiripentol (200 mg/kg) plus Phenytoin (60 mg/kg) |

III. Results

1. Phenytoin Teratogenicity

The primary focus of the study was to determine whether the co-administration of stiripentol with phenytoin could reduce the reproductive risks (teratogenicity) inherent in phenytoin monotherapy. The results presented in Table 2 represent the percent of total fetal abnormalities, both skeletal and soft tissue defects, observed in the offspring of dams assigned to each of the test groups. In year I, phenytoin induced statistically significant increases in the malformation rates in the SWV and C57 fetuses at both dosages (P<0.05). A significant increase in malformations was observed in the LM/Bc strain only at the high dosage in year I (P<0.05). In year II, phenytoin induced a significant increase in congenital abnormalities in all three strains at the high (60 mg/kg) dosage, when compared to the controls (P<0.05). In year II the low phenytoin treatment concentration (30 mg/kg) induced a statistically significant increase in malformations only in the C57 fetuses (P<0.05).

2. Control Groups and Stiripentol Group

There were no significant differences in malformations rates of groups 1, 2 and 5, indicating that the chronic oral administration of stiripentol was not teratogenic (P>0.05). These control groups were indistinguishable from each other in both year I and II, and therefore these results were not included in Table 2.

3. Reduction of Phenytoin Teratogenicity by Co-administrations of Stiripentol (i) In year I, a statistically significant reduction in fetal abnormalities was observed in the stiripentol/phenytoin combined treatment group, when compared to the phenytoin (30 mg/kg) monotherapy group in both the SWV and C57 strains (P<0.05). No protection could be determined in the LM/Bc strain, as the phenytoin (30 mg/kg) dose was not teratogenic in this strain.

(ii) In year II, this same protective effect could only be determined statistically for the C57 strain (P<0.05). Again, it was the lack of significant teratogenicity observed at the phenytoin (30 mg/kg) dosage in the LM/Bc and SWV strains that precluded any determination of a protective effect of stiripentol co-therapy.

(iii) A seventh treatment group was added in year II, with the dams receiving phenytoin (60 mg/kg) together with stiripentol (200 mg/kg) to determine whether or not stiripentol co-treatment would be protective relative to a high dosage of phenytoin (60 mg/kg). This combined treatment significantly reduced the incidence of fetal defects in the SWV and LM/Bc mouse strains (P<0.05).

4. Other Maternal and Fetal Parameters

A number of maternal and fetal test parameters were measured, including the number of implantations, resorptions, mean fetal weight and plasma drug concentrations. In both years I and II, there was no significant differences between the treatment groups in either the number of implantation sites or the rate that the conceptuses were reabsorbed within each strain irrespective of the drug treatment (P>0.05). In year I, in utero exposure to phenytoin did have a significant impact on fetal growth, as significant differences in fetal weights were observed in the SWV strain at both phenytoin dosages, and in the C57 mice at the 60 mg/kg treatment (P<0.05). No significant differences in fetal weights were observed in the LM/Bc strain in year I. There were no significant differences observed in the mean fetal weights in any strain in year II of the study (P>0.05).

TABLE 2

Reduction in phenytoin teratogenicity by co-administration of stiripentol

| Treatment | SWV Yr I | SWV Yr II | LM/Bc Yr I | LM/Bc Yr II | C57BL/6J Yr I | C57BL/6J Yr II |
| --- | --- | --- | --- | --- | --- | --- |
| PHT (60) | | | | | | |
| % Abn[1] | 46.1 | 43.1 | 30.4 | 29.4 | 55.4 | 34.7 |
| µg/ml | 15.5 | 12.6 | 13.2 | 9.9 | 13.1 | 7.1 |
| PHT (30) | | | | | | |
| % Abn[1] | 33.0 | 15.1 | 7.5 | 12.9 | 36.5 | 23.4 |
| µg/ml | 4.2 | 4.6 | 8.0 | 3.7 | 6.6 | 5.1 |
| PHT (30) STP | | | | | | |
| % Abn[1] | 8.7 | 8.8 | 7.4 | 8.8 | 13.0 | 13.3 |
| µg/ml | 5.6 | 5.3 | 5.9 | 3.8 | 5.5 | 4.0 |
| PHT (60) STP | | | | | | |
| % Abn[1] | —[2] | 16.7 | —[2] | 13.7 | —[2] | 12.3 |

[1] % Abn = percent abnormal
[2] this group was not included in year 1

These studies show that stiripentol significantly reduces the teratogenicity of a classic antiepileptic drug such as phenytoin.

EXAMPLE 2

| Capsules containing: | |
| --- | --- |
| stiripentol | 500 mg |
| magnesium stearate | 3 mg |

EXAMPLE 3

| Capsules containing: | |
|---|---|
| stiripentol | 500 mg |
| phenytoin | 100 mg |
| magnesium stearate | 3 mg |

We claim:

1. A method for treating epilepsy in a female patient which comprises administering a therapeutically effective amount of a drug selected from the group consisting of phenytoin, carbamazepine, valproic acid and sodium valproate, together with the coadministration of stiripentol whereby teratogenic effects of said drug are avoided.

2. The method of claim 1, wherein the daily oral dosage is 5–100 mg/kg.

3. The method of claim 1, wherein the daily oral dosage is 10–50 mg/kg.

* * * * *